United States Patent

(12) United States Patent
Katsevich

(10) Patent No.: US 6,574,299 B1
(45) Date of Patent: Jun. 3, 2003

(54) EXACT FILTERED BACK PROJECTION (FBP) ALGORITHM FOR SPIRAL COMPUTER TOMOGRAPHY

(75) Inventor: Alexander Katsevich, Oviedo, FL (US)

(73) Assignee: University of Central Florida, Orlando, FL (US)

( * ) Notice: Subject to any disclaimer, the term of this patent is extended or adjusted under 35 U.S.C. 154(b) by 0 days.

(21) Appl. No.: 10/143,160

(22) Filed: May 10, 2002

Related U.S. Application Data

(60) Provisional application No. 60/312,827, filed on Aug. 16, 2001.

(51) Int. Cl.$^7$ .................................................. A61B 6/03
(52) U.S. Cl. ......................................... 378/15; 378/901
(58) Field of Search ............................ 378/4, 8, 15, 19, 378/901

(56) References Cited

U.S. PATENT DOCUMENTS

| | | | | |
|---|---|---|---|---|
| 5,663,995 | A | 9/1997 | Hu | 378/15 |
| 5,706,325 | A | 1/1998 | Hu | 378/4 |
| 5,784,481 | A | 7/1998 | Hu | 382/131 |
| 5,881,123 | A | 3/1999 | Tam | 378/4 |
| 5,926,521 | A | 7/1999 | Tam | 378/4 |
| 5,960,055 | A | 9/1999 | Samarasekera et al. | 378/4 |
| 5,995,580 | A | 11/1999 | Schaller | 378/15 |
| 6,009,142 | A | 12/1999 | Sauer et al. | 378/15 |
| 6,014,419 | A | 1/2000 | Hu | 378/4 |
| 6,072,851 | A | 6/2000 | Sivers | 378/15 |
| 6,130,930 | A | * 10/2000 | Tam | 378/4 |
| 6,173,032 | B1 | 1/2001 | Besson | 378/19 |
| 6,198,789 | B1 | 3/2001 | Dafni | 378/8 |
| 6,215,841 | B1 | 4/2001 | Hsieh | 378/8 |
| 6,233,303 | B1 | 5/2001 | Tam | 378/4 |
| 6,266,388 | B1 | 7/2001 | Hsieh | 378/8 |
| 6,459,754 | B1 | * 10/2002 | Besson et al. | 378/4 |

OTHER PUBLICATIONS

Kachelrie, Et Al., *Advanced Single–Slice Rebining in Cone–Beam Spiral CT*. Med. Phys. 27 (4), Apr. 2000, P 754–772.
Bruder, Et Al., *Single–Slice Rebinning Reconstruction in Spiral Cone–Beam Computer Tomography*, IEEE V. 19, No. 9 Sep. 2000, P 873–887.
Schaller, Et Al., *Exact Radon Rebinning Algorithm for the Long Object Problem in Helical Cone–Beam CT*, IEEE, vol. 19 No. 5, May 2000, P 361–375.
Turbell, Et Al., *Helical Cone–Beam Tomography*, 2000 John Wiley & Sons, Inc. P. 91–100.
Defrise, Et Al., *A Solution to the Long–Object Problem in Helical Cone–Beam Tomography*, Phys, Med. Biol.45 (2000) P 623–643.
Noo, Et Al., *Approximate Short–Scan Filtered–BackProjection for Helical CB Reconstruction*, IEEE 1999, P. 2073–2077.
Kudo, Et Al., *A New Approach to Exact Cone–Beam Reconstruction Without Radon Transfer*, IEEE, 1999 PG. 1636–1643.

* cited by examiner

*Primary Examiner*—David V. Bruce
(74) *Attorney, Agent, or Firm*—Brian S. Steinberger; Law Offices of Brian S. Steinberger, P.A.

(57) ABSTRACT

Reconstructing images of objects spirally scanned with two-dimensional detectors with a novel algorithm. The image reconstruction process is proven to create an exact image of the object under the ideal circumstances. The algorithm has an FBP (Filtered Back Projection) structure and works very efficiently. The algorithm uses less computer power and combines the benefits of Exact Algorithms and Approximate algorithms.

20 Claims, 10 Drawing Sheets

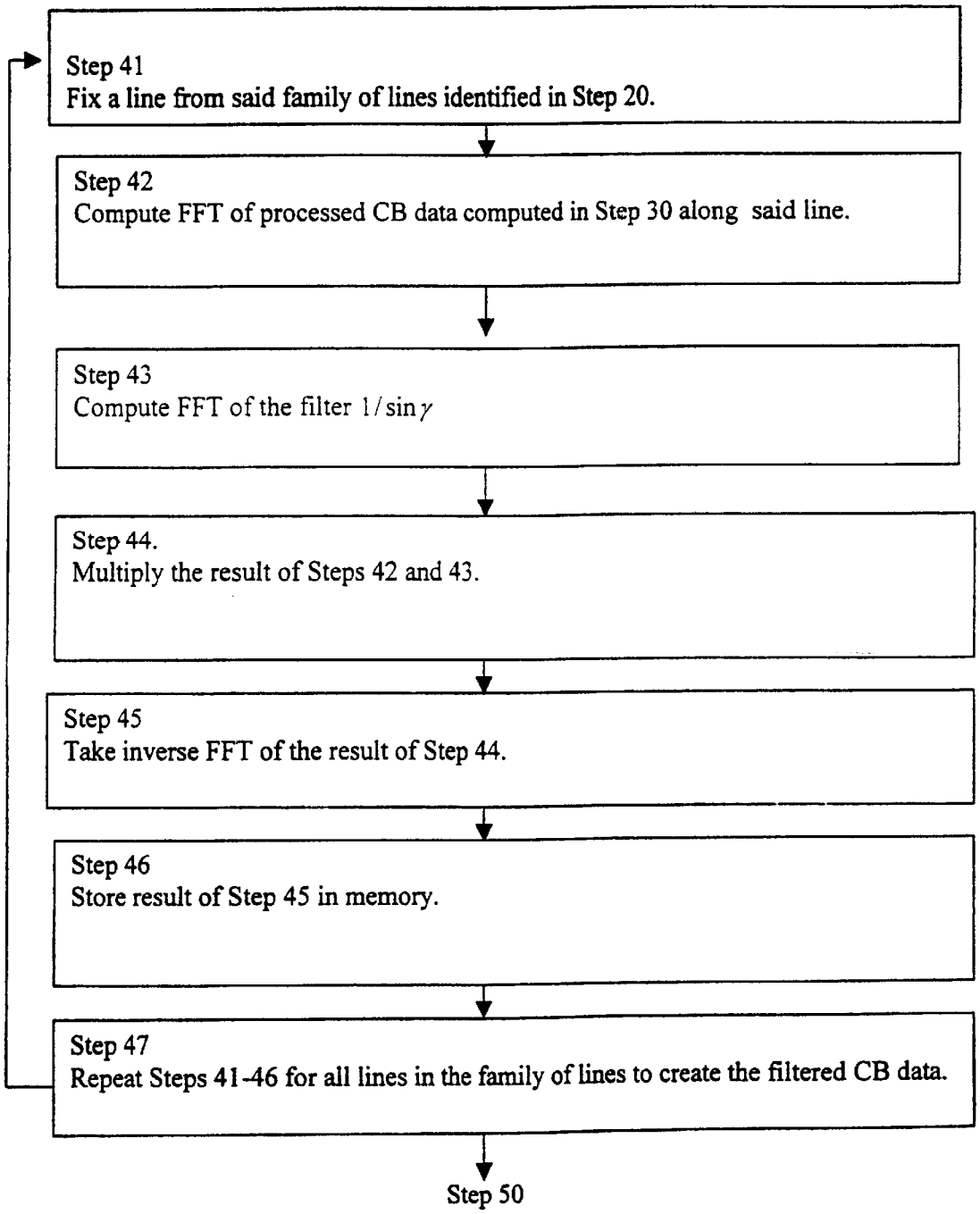

Fig. 11

Step 50. Back-projection

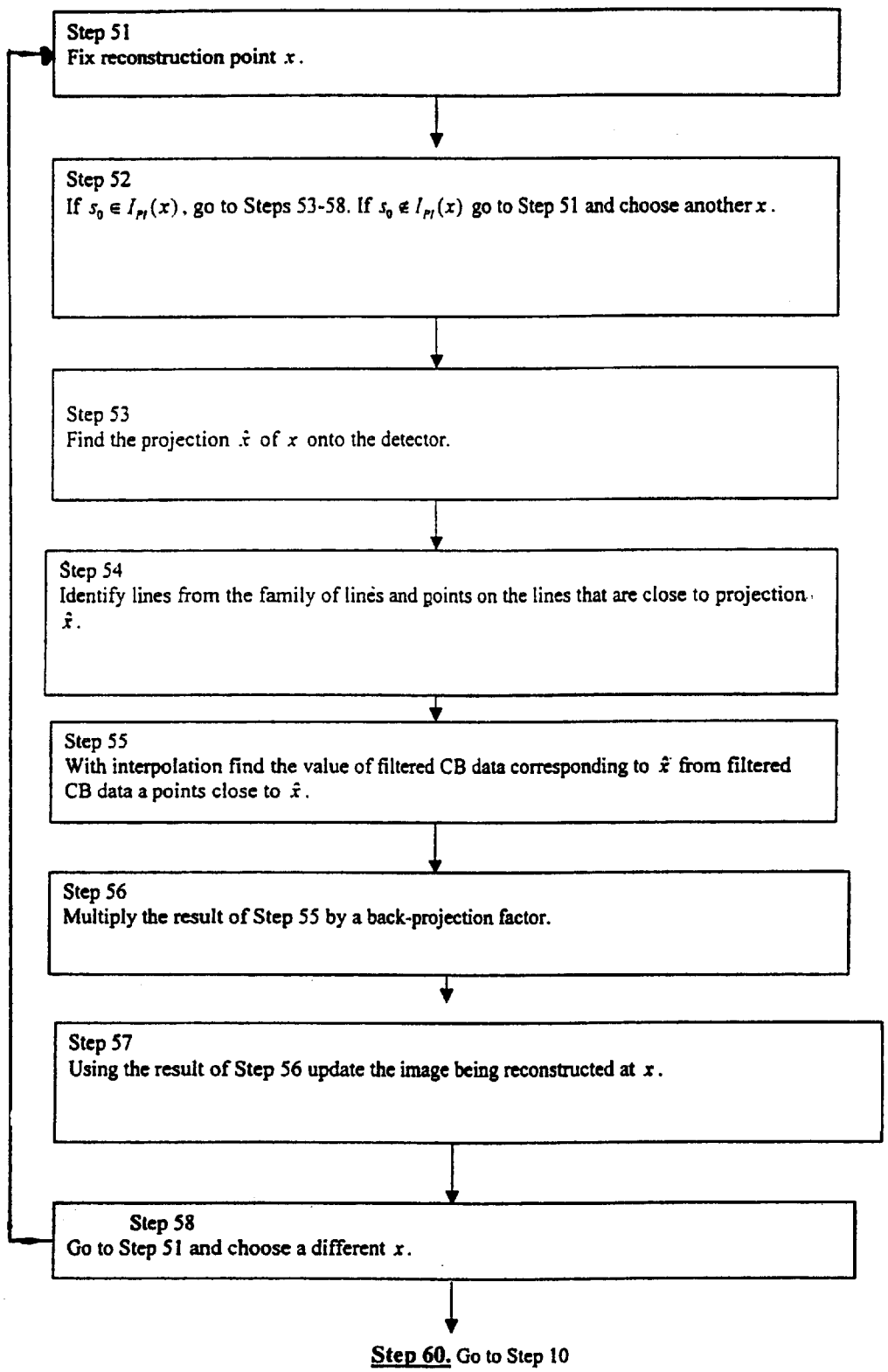

Step 51
Fix reconstruction point $x$.

Step 52
If $s_0 \in I_{pi}(x)$, go to Steps 53-58. If $s_0 \notin I_{pi}(x)$ go to Step 51 and choose another $x$.

Step 53
Find the projection $\hat{x}$ of $x$ onto the detector.

Step 54
Identify lines from the family of lines and points on the lines that are close to projection $\hat{x}$.

Step 55
With interpolation find the value of filtered CB data corresponding to $\hat{x}$ from filtered CB data a points close to $\hat{x}$.

Step 56
Multiply the result of Step 55 by a back-projection factor.

Step 57
Using the result of Step 56 update the image being reconstructed at $x$.

Step 58
Go to Step 51 and choose a different $x$.

Step 60. Go to Step 10

EXACT FILTERED BACK PROJECTION (FBP) ALGORITHM FOR SPIRAL COMPUTER TOMOGRAPHY

This invention relates to computer tomography, and in particular to processes and systems for reconstructing three dimensional images from the data obtained by a spiral scan, and this invention claims the benefit of priority to U.S. Provisional Application No. 60/312,827 filed Aug. 16, 2001.

BACKGROUND AND PRIOR ART

Over the last thirty years, computer tomography (CT) has gone from image reconstruction based on scanning in a slice-by-slice process to spiral scanning. From the 1970s to 1980s the slice-by-slice scanning was used. In this mode the incremental motions of the patient on the table through the gantry and the gantry rotations were performed one after another. Since the patient was stationary during the gantry rotations, the trajectory of the x-ray source around the patient was circular. Pre-selected slices through the patient have been reconstructed using the data obtained by such circular scans. From the mid 1980s to present day, spiral type scanning has become the preferred process for data collection in CT. Under spiral scanning a table with the patient continuously moves through the gantry that is continuously rotating about the table. At first, spiral scanning has used one-dimensional detectors, which receive data in one dimension (a single row of detectors). Later, two-dimensional detectors, where multiple rows (two or more rows) of detectors sit next to one another, have been introduced. In CT there have been significant problems for image reconstruction especially for two-dimensional detectors. In what follows the data provided by the two-dimensional detectors will be referred to as cone-beam (CB) data or CB projections.

For three-dimensional (also known as volumetric) image reconstruction from the data provided by a spiral scan with two-dimensional detectors, there are two known groups of algorithms: Exact algorithms and Approximate algorithms, that each have known problems. Under ideal circumstances, exact algorithms can provide a replication of an exact image. Thus, one should expect that exact algorithms would produce images of good quality even under non-ideal (that is, realistic) circumstances. However, exact algorithms can be known to take many hours to provide an image reconstruction, and can take up great amounts of computer power when being used. These algorithms can require keeping considerable amounts of cone beam projections in memory. Additionally, some exact algorithms can require large detector arrays to be operable and can have limits on the size of the patient being scanned.

Approximate algorithms possess a filtered back projection (FBP) structure, so they can produce an image very efficiently and using less computing power than Exact algorithms. However, even under the ideal circumstances they produce an approximate image that may be similar to but still different from the exact image. In particular, Approximate algorithms can create artifacts, which are false features in an image. Under certain circumstances these artifacts could be quite severe.

To date, there are no known algorithms that can combine the beneficial attributes of Exact and Approximate algorithms into a single algorithm that is capable of replicating an exact image under the ideal circumstances, uses small amounts of computer power, and reconstructs the exact images in an efficient manner (i.e., using the FBP structure). Here and everywhere below by the phrase that the algorithm of the invention reconstructs an exact image we will mean that in theory the algorithm is capable of reconstructing an exact image. Since in real life any data contains noise and other imperfections, no algorithm is capable of reconstructing an exact image.

Image reconstruction has been proposed in many U.S. Patents. See for example, U.S. Pat. Nos. 5,663,995 and 5,706,325 and 5,784,481 and 6,014,419 to Hu; U.S. Pat. Nos. 5,881,123 and 5,926,521 and 6,130,930 and 6,233,303 to Tam; U.S. Pat. No. 5,960,055 to Samaresekera et al.; U.S. Pat. No. 5,995,580 to Schaller; U.S. Pat. No. 6,009,142 to Sauer; U.S. Pat. No. 6,072,851 to Sivers; U.S. Pat. No. 6,173,032 to Besson; U.S. Pat. No. 6,198,789 to Dafni; U.S. Pat. Nos. 6,215,841 and 6,266,388 to Hsieh. However, none of the patents overcome all of the deficiencies to image reconstruction referenced above.

SUMMARY OF THE INVENTION

A primary objective of the invention is to provide an improved process and system for reconstructing images of objects that have been scanned in a spiral fashion with two-dimensional detectors.

A secondary objective of the invention is to provide an improved process and system for reconstructing images of spirally scanned objects that is known to theoretically be able to reconstruct an exact image and not an approximate image.

A third objective of the invention is to provide an improved process and system for reconstructing images of spirally scanned objects that creates an exact image in an efficient manner using a filtered back projection (FBP) structure.

A fourth objective of the invention is to provide an improved process and system for reconstructing images of spirally scanned objects that creates an exact image with minimal computer power.

A fifth objective of the invention is to provide an improved process and system for reconstructing images of spirally scanned objects that creates an exact image with an FBP structure.

A sixth objective of the invention is to provide an improved process and system for reconstructing images of spirally scanned objects with larger pitch, leading to faster scans than previous techniques.

A seventh objective of the invention is to provide an improved process and system for reconstructing images of spirally scanned objects which take less time than current techniques, thereby allowing use in everyday clinical applications.

An eighth objective of the invention is to provide an improved process and system for reconstructing images of spirally scanned objects that is CB projection driven allowing for the algorithm to work simultaneously with the CB data acquisition.

A ninth objective of the invention is to provide an improved process and system for reconstructing images of spirally scanned objects that does not requiring storage for numerous CB projections in computer memory.

A tenth objective of the invention is to provide an improved process and system for reconstructing images of spirally scanned objects that allows for almost real time imaging to occur where images are displayed as soon as a slice measurement is completed.

A first preferred embodiment of the invention uses a six overall step process for reconstructing the image of an object under a spiral scan. In a first step a current CB projection is measured. Next, a family of lines is identified on a detector according to a novel algorithm. Next, a computation of derivatives between neighboring projections occurs and is followed by a convolution of the derivatives with a filter along lines from the selected family of line. Next, using the filtered data, the image is updated by performing back projection. Finally, the preceding steps are repeated for each CB projection until an entire object has been scanned. This embodiment works with keeping several (approximately 2–4) CB projections in memory at a time and uses one family of lines.

For the second embodiment, the novel algorithm allows for one CB projection to be kept in memory at a time and one family of lines is used.

For the third embodiment, two families of lines can be used in combination with either one CB projection in memory or with several CB projections in memory.

Further objects and advantages of this invention will be apparent from the following detailed description of a presently preferred embodiment, which is illustrated schematically in the accompanying drawings.

BRIEF DESCRIPTION OF THE FIGURES

FIG. 10 is a seven substep flow chart for filtering, which corresponds to step 40 of FIG. 2.

FIG. 11 is an eight substep flow chart for backprojection, which corresponds to step 50 of FIG. 2.

DESCRIPTION OF THE PREFERRED EMBODIMENTS

Before explaining the disclosed embodiments of the present invention in detail it is to be understood that the invention is not limited in its application to the details of the particular arrangement shown since the invention is capable of other embodiments. Also, the terminology used herein is for the purpose of description and not of limitation.

FIRST EMBODIMENT

Figure 1:
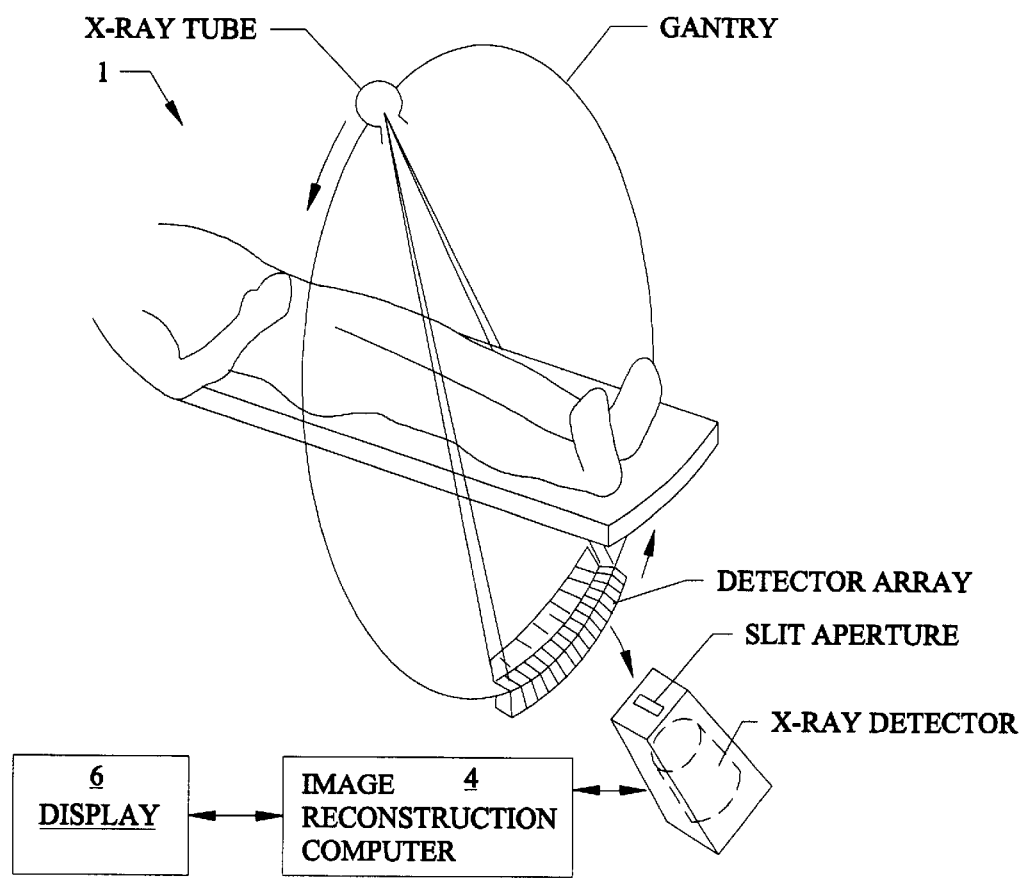
FIG. 1 shows a typical arrangement of a patient on a table that moves within a rotating gantry having an x-ray tube source and a detector array, where cone beam projection data sets are received by the x-ray detector, and an image reconstruction process takes place in a computer with a display for the reconstructed image.

FIG. 1 shows a typical arrangement of a patient on a table that moves within a rotating gantry having an x-ray tube source and a detector array, where CB projections are received by the x-ray detector, and an image reconstruction process takes place in a computer 4 with a display 6 for displaying the reconstructed image. For the subject invention, the detector array is a two-dimensional detector array. For example, the array can include two, three or more rows of plural detectors in each row. If three rows are used with each row having ten detectors, then one CB projection set would be thirty individual x-ray detections.

Figure 2:
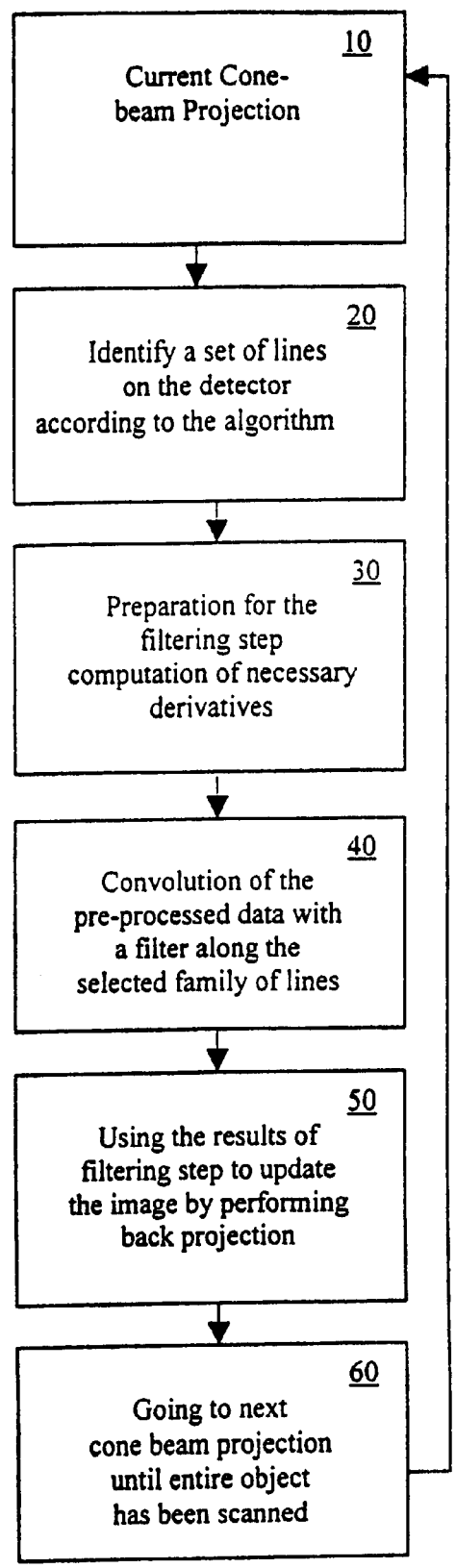
FIG. 2 shows an overview of the basic process steps of the invention.

FIG. 2 shows an overview of the basic process steps of the invention that occur during the image reconstruction process occurring in the computer 4 using a first embodiment.

The first embodiment works with keeping several (approximately 2–4) CB projections in computer memory at a time and uses one family of lines.

In the first step 10, a current CB projection set is taken. The next step 20 identifies a set of lines on a virtual x-ray detector array according to the novel algorithm, which will be explained later in greater detail. In the given description of the algorithm it is assumed that the detector array is flat, so the selected line can be a straight tilted line across the array.

The next step 30 is the preparation for the filtering step, which includes computations of the necessary derivative of the CB projection data for the selected lines.

The next step 40 is the convolution of the computed derivative (the processed CB data) with a filter along lines from the selected family of lines. This step can also be described as shift-invariant filtering of the derivative of the CB projection data. In the next step 50, the image of the object being computed is updated by performing back projection.

The invention will now be described in more detail by first describing the main inversion formula followed by the novel algorithm.

Figure 3:
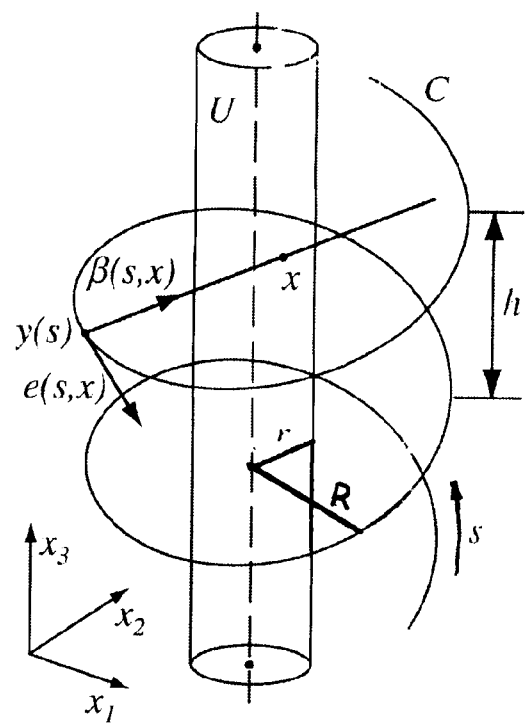
FIG. 3 shows mathematical notations of the spiral scan about the object being scanned.

The spiral path C of the x-ray source is described by the following equations and depicted in FIG. 3, which shows mathematical notations of the spiral scan about the object being scanned:

$$y_1(s)=R\cos(s),\ y_2(s)=R\sin(s),\ y_3(s)=s(h/2\pi), \quad (1)$$

Here
s is a real parameter;
h is pitch of the spiral;
R is distance from the x-ray source to the isocenter.
The object being scanned is located inside an imaginary cylinder U of radius r, r<R (see FIG. 3). Let $\psi$ be a smooth function with the properties $$\psi(0)=0;\ 0<\psi'(t)<1,\ t\in[0,2\pi]. \quad (2)$$

Even though it is not necessary, we will assume in addition that $$\psi'(0)=0.5;\ \psi^{(2k+1)}(0)=0,\ k\geq 1. \quad (3)$$

Here and in what follows we assume that $s_0$, $s_1$, and $s_2$ are always related by $$s_1=\psi(s_2-s_0)+s_0\ \text{if}\ s_0\leq s_2<s_0+2\pi, \quad (4)$$

$$s_1=\psi(s_0-s_2)+s_2\ \text{if}\ s_0-2\pi<s_2<s_0. \quad (5)$$

Conditions (2) and (3) can be easily satisfied. One can take, for example, $\psi(t)=t/2$, and this leads to $$s_1=(s_0+s_2)/2,\ s_0-2\pi<s_2<s_0+2\pi. \qquad (6)$$

Denote $$u(s_0, s_2) = \qquad (7)$$
$$\frac{(y(s_1) - y(s_0)) \times (y(s_2) - y(s_0))}{|(y(s_1) - y(s_0)) \times (y(s_2) - y(s_0))|} \operatorname{sgn}(s_2 - s_0) \text{ if } 0 < |s_2 - s_0| < 2\pi,$$

$$u(s_0, s_2) = \frac{\dot{y}(s_0) \times \ddot{y}(s_0)}{|\dot{y}(s_0) \times \ddot{y}(s_0)|} \text{ if } s_2 = s_0. \qquad (8)$$

Here $y(s_0)$, $y(s_1)$, $y(s_2)$ are three points on the spiral related according to (4), (5);

$u(s_0, s_2)$ is a unit vector perpendicular to the plane containing the points $y(s_0)$, $y(s_1)$, $y(s_2)$;

$\dot{y}(s):=dy/ds$;

$\ddot{y}(s):=d^2y/ds^2$.

Figure 4:
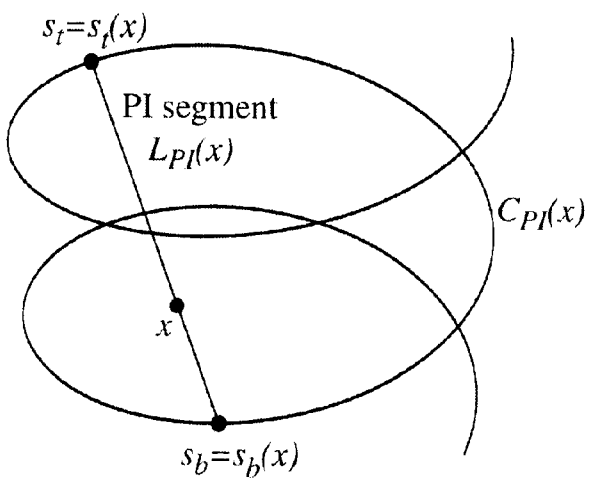
FIG. 4 illustrates a PI segment of an individual image reconstruction point.

It is known in the literature that any point strictly inside the spiral belongs to one and only one PI segment (see P. E. Danielsson et al. "Towards exact reconstruction for helical cone-beam scanning of long objects. A new detector arrangement and a new completeness condition" in "Proc. 1997 Meeting on Fully 3D Image Reconstruction in Radiology and Nuclear Medicine (Pittsburgh)", eds. D. W. Townsend and P. E. Kinahan, yr. 1997, pp. 141–144, and M. Defrise, F. Noo, and H. Kudo "A solution to the long-object problem in helical cone-beam tomography", Physics in Medicine and Biology, volume 45, yr. 2000, pp. 623–643). A PI segment is a segment of line endpoints of which are located on the spiral and separated by less than one pitch in the axial direction (see FIG. 4). Let $s=s_b(x)$ and $s=s_t(x)$ denote values of the parameter corresponding to the endpoints of the PI segment containing a reconstruction point x. We will call $I_{PI}(x):=[s_b(x),s_t(x)]$ the PI parametric interval. The part of the spiral corresponding to $I_{PI}(x)$ will be denoted $C_{PI}(x)$ (see FIG. 4 which illustrates a PI segment of an individual image reconstruction point). Next we fix a reconstruction point x inside the spiral and $s_0 \in I_{PI}(x)$. Find $s_2 \in I_{PI}(x)$ such that the plane through $y(s_0)$, $y(s_2)$, and $y(s_1(s_0,s_2))$ contains x. More precisely, we have to solve for $s_2$ the following equation $$(x-y(s_0)) \cdot u(s_0,s_2)=0,\ s_2 \in I_{PI}(x). \qquad (9)$$

Such $s_2$ exists, is unique, and depends smoothly on $s_0$. Therefore, this construction defines $s_2:=s_2(s_0,x)$ and, consequently, $u(s_0,x):=u(s_0,s_2(s_0,x))$. Equation (9) can be solved by a variety of methods, all known under the name "root finders". The main reconstruction formula now is as follows:

$$\left(f(x) = -\frac{1}{2\pi^2} \int_{I_{PI}(x)} \frac{1}{|x-y(s)|} \int_0^{2\pi} \frac{\partial}{\partial q} D_f(y(q), \Theta(s, x, \gamma))\bigg|_{q=s} \frac{d\gamma}{\sin\gamma}\right) ds, \qquad (10)$$

where f is the function representing the distribution of the x-ray attenuation coefficient inside the object being scanned, $e(s,x)=\beta(s,x) \times u(s,x)$, × is the cross-product of two vectors, $\Phi(s,x,\gamma):=\cos\gamma\beta(s,x)+\sin\gamma e(s,x)$, $D_f$ is the cone beam transform of f:

$$D_f(y, \Theta) = \int_0^\infty f(y + \Theta t) dt, \qquad (11)$$

$$\beta(s, x) := \frac{x - y(s)}{|x - y(s)|}$$

is the unit vector from the focal point y(s) pointing towards the reconstruction point x.

The proof that equation (10) gives a theoretically exact image is presented in A. Katsevich "Improved exact FBP algorithm for Spiral CT" submitted for possible publication to the journal "Advances in Applied Mathematics" in November 2001.

Now we describe an efficient (that is, of the FBP type) implementation of inversion formula (10). It is clear from (9) that $s_2(s,x)$ actually depends only on s and $\beta(s,x)$. Therefore, we can write $u(s,\beta):=u(s,s_2(s,\beta)),e(s,\beta):=\beta \times u(s,\beta),\beta \in S^2,$ $$\Psi(s, \beta) := \int_0^{2\pi} \frac{\partial}{\partial q} D_f(y(q), \cos\gamma\beta + \sin\gamma e(s, \beta))\bigg|_{q=s} \frac{1}{\sin\gamma} d\gamma, \qquad (12)$$

$$f(x) = -\frac{1}{2\pi^2} \int_{I_{PI}(x)} \frac{1}{|x-y(s)|} \Psi(s, \beta(s, x)) ds. \qquad (13)$$

Here $S^2$ is the unit sphere.

Figure 5:
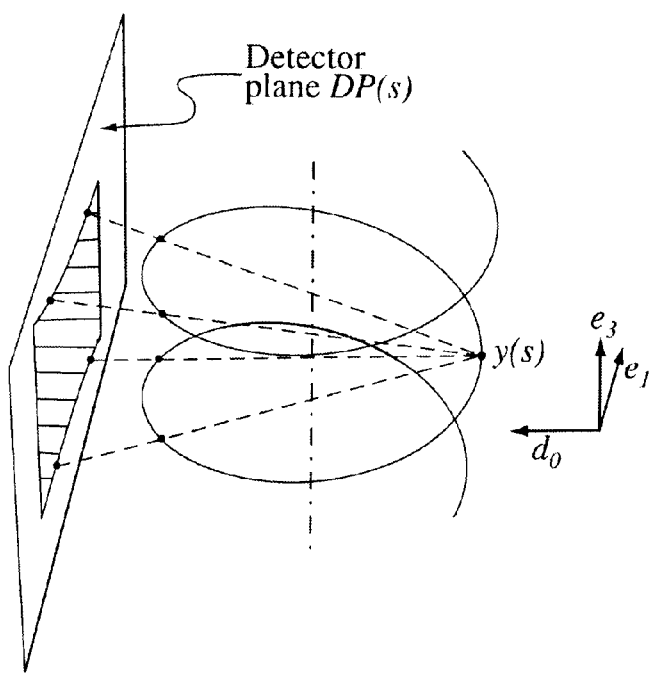
FIG. 5 illustrates a stereographic projection from the current source position on to the detector plane used in the algorithm for the invention.

To better understand equations (12), (13), we illustrate various important features on the detector array. Suppose first that the x-ray source is fixed at y(s) for some $s \in I_{PI}(x)$. Project stereographically the upper and lower turns of the spiral onto the detector plane as shown in FIG. 5 which illustrates a stereographic projection from the current source position on to the detector plane used in the algorithm for the invention.

Since the detector array rotates together with the source, the detector plane depends on s and is denoted DP(s). It is assumed that DP(s) is parallel to the axis of the spiral and is tangent to the cylinder $y_1^2+y_2^2=R^2$ (cf. equation (1)) at the point opposite to the source. Thus, the distance between y(s) and the detector plane is 2R. In order to make FIG. 5 more readable, the detector plane is drawn slightly away from the spiral. Introduce coordinates in the detector plane as follows. Let the $d_1$-axis be perpendicular to the axis of the spiral, and the $d_2$-axis—parallel to it. This gives the following parametric curves:

$$d_1(q) = 2R \frac{\sin(q-s)}{1-\cos(q-s)}, \qquad (14)$$

$$d_2(q) = \frac{h}{\pi} \frac{q-s}{1-\cos(q-s)},$$

Figure 6:
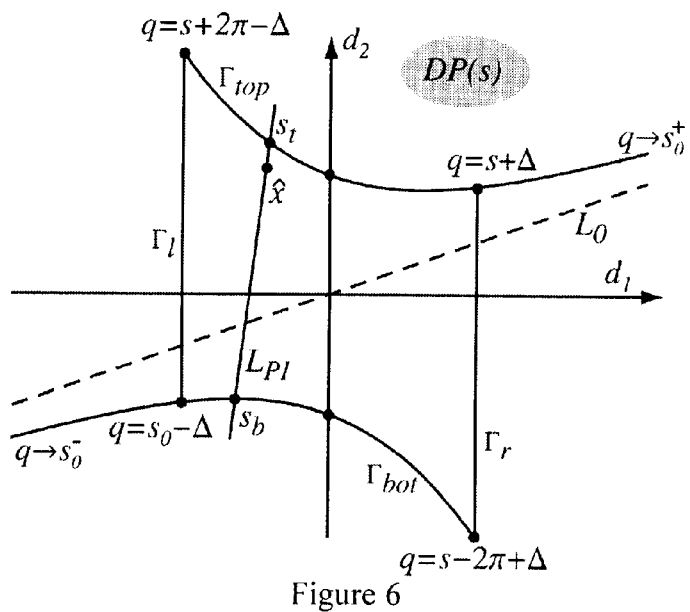
FIG. 6 illustrates various lines and curves, such as boundaries, on the detector plane.
Figure 7:
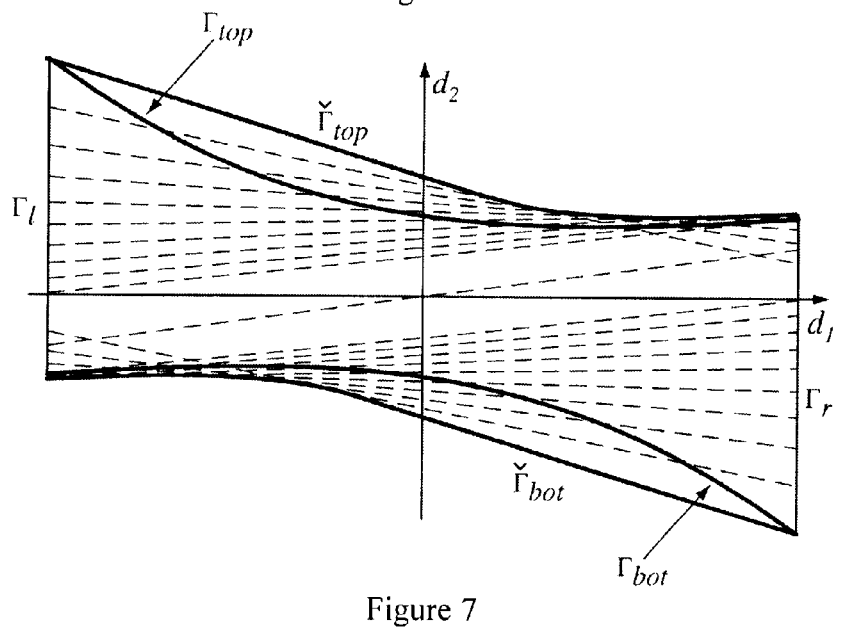
FIG. 7 illustrates a family of lines used in the algorithm of the invention.

$\Delta \leq q - s \leq 2\pi - \Delta$ or $\Delta - 2\pi \leq q - s \leq -\Delta,$ where $\Delta$ is determined by the radius r of the imaginary cylinder U inside which the patient is located (see FIG. 3): $\Delta=2\cos^{-1}(r/R)$. The top and bottom curves are denoted $\Gamma_{top}$ and $\Gamma_{bot}$, respectively (see FIG. 6 which illustrates various lines and curves, such as boundaries, on the detector plane). The common asymptote of $\Gamma_{top}$ and $\Gamma_{bot}$ is denoted $L_0$. Let $\hat{x}$ denote the projection of x. Since $s \in I_{PI}(x)$, $\hat{x}$ is projected into the area between $\Gamma_{top}$ and $\Gamma_{bot}$ (see FIG. 6). Fix $s_2 \in [s-2\pi+\Delta, s+2\pi-\Delta], s_2 \neq s$, and let $\Pi(s_2)$ denote the plane through $y(s)$, $y(s_2)$, and $y(s_1(s,s_2))$. If $s_2=s$, $\Pi(s_2)$ is determined by continuity and coincides with the plane through $y(s)$ and parallel to $\dot{y}(s), \ddot{y}(s)$. The family of lines $L(s_2)$ obtained by intersecting $\Pi(s_2)$ with the detector plane is shown in FIG. 7.

By construction, given any $x \in U$ with $\beta(s,x)$ parallel to $\Pi(s_2)$ and such that $\hat{x}$ appears to the left (right) of the point of where the line $L(s_2)$ intersects $\Gamma_{top}$ ($\Gamma_{bot}$) for the first time if $\hat{x}$ is above (below) $L_0$, $s_2$ used here is precisely the same as $s_2$ found by solving (9). The condition that we have formulated regarding the location of $\hat{x}$ relative to $s_2$ and $L_0$ guarantees that $s_2 \in I_{PI}(x)$. Since $e(s,\beta) \cdot \beta = 0, |e(s,\beta)|=1$, we can write:

$$\beta=(\cos\theta,\sin\theta); e(s,\beta)=(-\sin\theta,\cos\theta); \beta,e(s,\beta) \in \Pi(s_2). \quad (15)$$

Therefore, $$\Psi(s,\beta) = \int_0^{2\pi} \frac{\partial}{\partial q} D_f(y(q),(\cos(\theta+\gamma),\sin(\theta+\gamma)))\bigg|_{q=s} \frac{1}{\sin\gamma} d\gamma, \quad (16)$$

$$\beta \in \prod(s_2).$$

Equation (16) is of convolution type and one application of Fast Fourier Transform (FFT) gives values of $\Psi(s,\beta)$ for all $\beta \in \Pi(s_2)$ at once.

Equations (13) and (16) would represent that the resulting algorithm is of the FBP type. This means that processing of every CB projection consists of two steps. First, shift-invariant and x-independent filtering along a family of lines on the detector is performed. Second, the result is back-projected to update the image matrix. The main property of the back-projection step is that for any point $\hat{x}$ on the detector the value obtained by filtering at $\hat{x}$ is used for all points x on the line segment connecting the current source position $y(s)$ with $\hat{x}$. Since $\partial/\partial q$ in (16) is a local operation, each CB projection is stored in memory as soon as it has been acquired for a short period of time for computing this derivative at a few nearby points and is never used later.

Now we describe the algorithm in detail following the six steps 10–60 shown in FIG. 2.

Step 10. Load the current CB(cone beam) projection into computer memory. Suppose that the mid point of the CB projections currently stored in memory is $y(s_0)$. The detector plane corresponding to the x-ray source located at $y(s_0)$ is denoted $DP(s_0)$.

Figure 8:
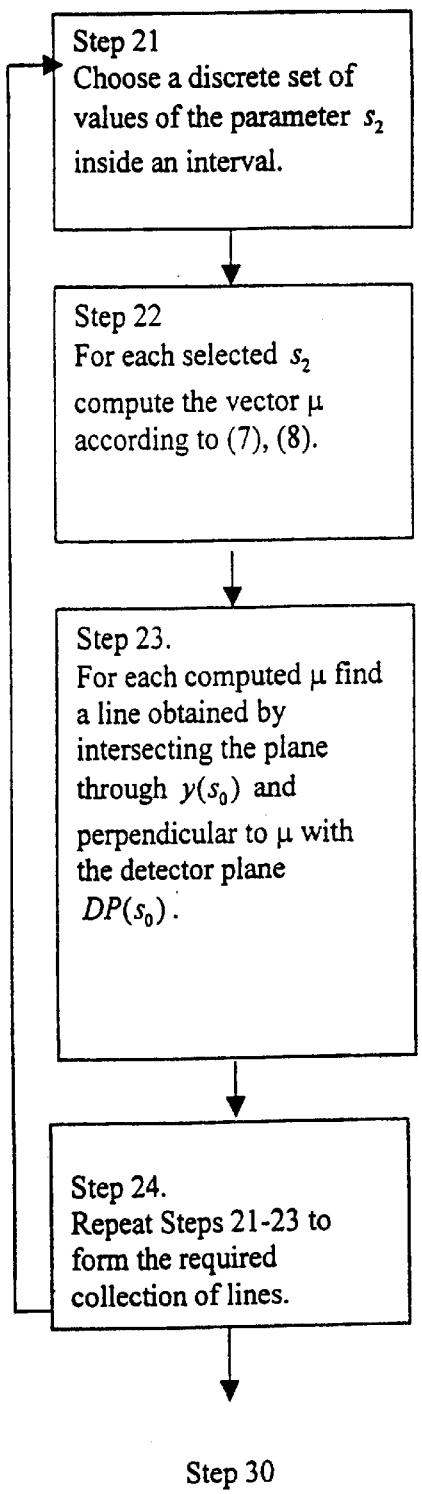
FIG. 8 is a four substep flow chart for identifying the set of lines, which corresponds to step 20 of FIG. 2.

Step 20. FIG. 8 is a four substep flow chart for identifying the set of lines, which corresponds to step 20 of FIG. 2. Referring to FIG. 8, the set of lines can be selected by the following substeps 21, 22, 23 and 24.

Step 21. Choose a discrete set of values of the parameter $s_2$ inside the interval $[s_0-2\pi+\Delta, s_0+2\pi-\Delta]$.

Step 22. For each selected $s_2$ compute the vector $u(s_0,s_2)$ according to equations (7), (8).

Step 23. For each $u(s_0,s_2)$ computed in Step 22 find a line which is obtained by intersecting the plane through $y(s_0)$ and perpendicular to the said vector $u(s_0,s_2)$ with the detector plane $DP(s_0)$.

Step 24. The collection of lines constructed in Step 23 is the required set of lines (see FIG. 7 which illustrates a family of lines used in the algorithm of the invention).

Step 30. Preparation for Filtering

Figure 9:
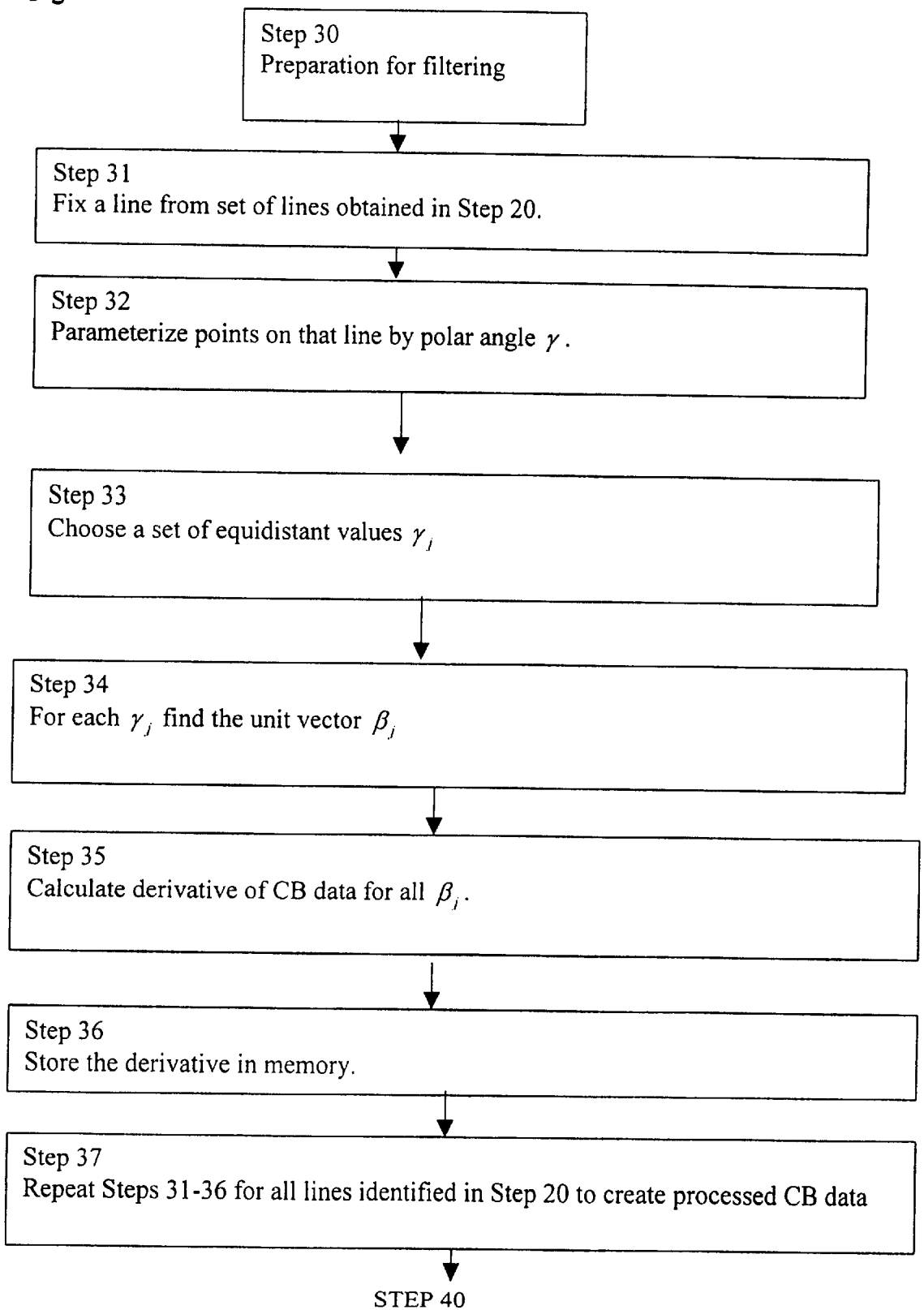
FIG. 9 is a seven substep flow chart for preparation for filtering, which corresponds to step 30 of FIG. 2.

FIG. 9 is a seven substep flow chart for preparation for filtering, which corresponds to step 30 of FIG. 2, which will now be described.

Step 31. Fix a line $L(s_2)$ from the said set of lines obtained in Step 20.

Step 32. Parameterize points on the said line by polar angle $\gamma$ in the plane through $y(s_0)$ and $L(s_2)$.

Step 33. Choose a discrete set of equidistant values $\gamma_j$ that will be used later for discrete filtering in Step 40.

Step 34. For each $\gamma_j$ find the unit vector $\beta_j$ which points from $y(s_0)$ towards the point on $L(s_2)$ that corresponds to $\gamma_j$.

Step 35. Using the CB projection data $D_f(y(q),\Phi)$ for a few values of q close to $s_0$ find numerically the derivative $(\partial/\partial q)D_f(y(q),\Phi)|_{q=s_0}$ for all $\Phi=\beta_j$.

Step 36. Store the computed values of the derivative in computer memory.

Step 37. Repeat Steps 31–36 for all lines $L(s_2)$ identified in Step 20. This way we will create the processed CB data $\Psi(s_0,\beta_j)$ corresponding to the x-ray source located at $y(s_0)$.

Step 40. Filtering

FIG. 10 is a seven substep flow chart for filtering, which corresponds to step 40 of FIG. 2, which will now be described.

Step 41. Fix a line from the said family of lines identified in Step 20.

Step 42. Compute FFT of the values of the said processed CB data computed in Step 30 along the said line.

Step 43. Compute FFT of the filter $1/\sin\gamma$.

Step 44. Multiply FFT of the filter $1/\sin\gamma$ (the result of Steps 43) and FFT of the values of the said processed CB data (the result of Steps 42).

Step 45. Take the inverse FFT of the result of Step 44.

Step 46. Store the result of Step 45 in computer memory.

Step 47. Repeat Steps 41–46 for all lines in the said family of lines. This will give the filtered CB data $\Phi(s_0,\beta_j)$.

By itself the filtering step is well known in the field and can be implemented, for example, as shown and described in U.S. Pat. No. 5,881,123 to Tam, which is incorporated by reference.

Step 50. Back-projection

FIG. 11 is an eight substep flow chart for backprojection, which corresponds to step 50 of FIG. 2, which will now be described.

Step 51. Fix a reconstruction point x, which represents a point inside the patient where it is required to reconstruct the image.

Step 52. If $s_0$ belongs to $I_{PI}(x)$, then the said filtered CB data affects the image at x and one performs Steps 53–58. If so is not inside the interval $I_{PI}(x)$, then the said filtered CB data is not used for image reconstruction at x. In this case go back to Step 51 and choose another reconstruction point.

Step 53. Find the projection $\hat{x}$ of x onto the detector plane $DP(s_0)$ and the unit vector $\beta(s_0,x)$, which points from $y(s_0)$ towards x.

Step 54. Using equation (9) identify the lines from the said family of lines and points on the said lines that are close to the said projection $\hat{x}$. This will give a few values of $\Phi(s_0,\beta_j)$ for $\beta_j$ close to $\beta(s_0,x)$.

Step 55. With interpolation estimate the value of $\Phi(s_0,\beta(s_0,x))$ from the said values of $\Phi(s_0,\beta_j)$ for $\beta_j$ close to $\beta(s_0,x)$.

Step 56. Compute the contribution from the said filtered CB data to the image being reconstructed at the point x by dividing $\Phi(s_0,\beta(s_0,x))$ by $-2\pi^2|x-y(s_0)|$.

Step 57. Add the said contribution to the image being reconstructed at the point x according to a pre-selected scheme (for example, the Trapezoidal scheme) for approximate evaluation of the integral in equation (15).

Step 58. Go to Step 51 and choose a different reconstruction point x.

Step 60. Go to Step 10 (FIG. 2) and load the next CB projection into computer memory.

The image can be displayed at all reconstruction points x for which the image reconstruction process has been completed (that is, all the subsequent CB projections are not needed for reconstructing the image at those points). Discard from the computer memory all the CB projections that are not needed for image reconstruction at points where the image reconstruction process has not completed. The algorithm concludes when the scan is finished or the image reconstruction process has completed at all the required points.

EMBODIMENT TWO

For the second embodiment, one CB (cone beam) projection can be kept in memory at a time and, as before, only one family of lines on the detector is used. Now we describe the second embodiment of the invention in detail. Integrating by parts with respect to s in equation (10) we obtain an inversion formula in which all the derivatives are performed with respect to the angular variables.

$$\left(f(x) = -\frac{1}{2\pi^2}\left(\left\{\left[\frac{1}{|x-y(s)|}\int_0^{2\pi} D_f(y(s),\Theta(s,x,\gamma))\frac{d\gamma}{\sin\gamma}\right]\right\}\right|_{s=s_b(x)}^{s=s_t(x)} - \right.$$
$$\int_{I_{Pl}(x)} \left(\frac{\partial}{\partial s}\frac{1}{|x-y(s)|}\right)\int_0^{2\pi} D_f(y(s),\Theta(s,x,\gamma))\frac{d\gamma}{\sin\gamma} ds -$$
$$\int_{I_{Pl}(x)} \frac{\beta_s(s,x)\cdot u(s,x)}{|x-y(s)|} \int_0^{2\pi} (\nabla_{u(s,x)}D_f)(y(s),\Theta(s,x,\gamma))\cot(\gamma)d\gamma ds -$$
$$\int_{I_{Pl}(x)} \frac{e_s(s,x)\cdot u(s,x)}{|x-y(s)|} \int_0^{2\pi} (\nabla_{u(s,x)}D_f)(y(s),\Theta(s,x,\gamma))d\gamma ds -$$
$$\left.\int_{I_{Pl}(x)} \frac{\beta_s(s,x)\cdot e(s,x)}{|x-y(s)|} \int_0^{2\pi} \left(\frac{\partial}{\partial\gamma}D_f(y(s),\Theta(s,x,\gamma))\right)\frac{d\gamma}{\sin\gamma} ds\right\}. \quad (17)$$

Here
$\beta_s = \partial\beta/\partial s$;
$e_s = \partial e/\partial s$, and
$\nabla_u D_f$ denotes the derivative of $D_f$ with respect to the angular variables along the direction of the vector u:

$$(\nabla_u D_f)(y(s),\Theta) = \frac{\partial}{\partial t}D_f(y(s),\sqrt{1-t^2}\,\Theta+tu)\bigg|_{t=0}, \Theta\in u^\perp. \quad (18)$$

Comparing equation (10) and equation (17) we see that equation (17) admits absolutely analogous filtered back-projection implementation. Moreover, since no derivative with respect to the parameter along the spiral is present, there is never a need to keep more than one CB projection in computer memory at a time. Now we describe the algorithm in detail.

Step 10. Load the current CB projection into computer memory and discard the CB projection that was in computer memory before. Suppose that the CB projection just loaded into computer memory corresponds to the x-ray source located at y(s).

Step 20 is the same as Step 20 in Embodiment One with $s_0$ replaced by s.

Step 30. Preparation for Filtering

Steps 31–34 are the same as in Embodiment One with $s_0$ replaced by s.

Step 35. Using the CB projection data $D_f(y(s),\Phi)$ find $D_f(y(s),\beta_j)$ and the derivatives $(\nabla_{u(s,x)}D_f)(y(s),\Phi(s,x,\gamma))|_{\Phi=\beta_j}$ and $$\frac{\partial}{\partial\gamma}D_f(y(s),\Theta(s,x,\gamma))\bigg|_{\Theta=\beta_j}$$

for all $\beta_j$. This can be done using interpolation and finite differences.

Step 36. Store the values computed in Step 35 in computer memory.

Step 37. Repeat Steps 31–36 for all lines $L(s_2)$ identified in Step 20. This way we will create the processed CB data $D_f(y(s),\beta_j)$, $(\nabla_{u(s,x)}D_f)(y(s),\beta_j)$, and $$\frac{\partial}{\partial\gamma}D_f(y(s),\beta_j).$$

Step 40. Filtering

Step 41. Fix a line from the said family of lines identified in Step 20.

Step 42. Using FFT convolve the said processed CB data computed in Step 30 with filters $1/\sin\gamma$ and $\cot\gamma$ along the said line according to equation (17). This will give the following three kinds of the filtered CB data (see also equations (12), (15), and (16)):

$$\Psi_1(s,\beta) = \int_0^{2\pi} D_f(y(s),\cos\gamma\beta+\sin\gamma e(s,\beta))\frac{d\gamma}{\sin\gamma},$$

$$\Psi_2(s,\beta) = \int_0^{2\pi} (\nabla_{u(s,x)}D_f)(y(s),\cos\gamma\beta+\sin\gamma e(s,\beta))\cot(\gamma)d\gamma,$$

$$\Psi_3(s,\beta) = \int_0^{2\pi} \left(\frac{\partial}{\partial\gamma}D_f(y(s),\cos\gamma\beta+\sin\gamma e(s,\beta))\right)\frac{d\gamma}{\sin\gamma}$$

for all $\beta=\beta_j$. As before, by itself convolution with a filter is well known in the field and can be implemented, for example, as described in U.S. Pat. No. 5,881,123 to Tam, which is incorporated by reference.

Step 43. Using the processed CB data $(\nabla_{u(s,x)}D_f)(y(s),\beta_j)$ evaluate numerically the integral $$\Psi_4(s,\beta) = \int_0^{2\pi} (\nabla_{u(s,x)}D_f)(y(s),\cos\gamma\beta+\sin\gamma e(s,\beta))d\gamma.$$

Step 44. Store the results of Step 42 and 43 in computer memory.

Step 47. Repeat Steps 41–44 for all lines in the said family of lines.

Step 50. Back-projection

Steps 51–53 are the same as in Embodiment One with $s_0$ replaced by s.

Step 54. Using equation (9) identify the lines from the said family of lines and points on the said lines that are close to the said projection $\hat{x}$. This will give a few values of $\Psi(s,\beta_j)$, $k=1,2,3,4$, for $\beta_j$ close to $\beta(s,x)$.

Step 55. With interpolation compute the quantities $\Psi_k(s, \beta(s,x))$, k=1,2,3,4, from the said values $\Psi_k(s,\beta_j)$, k=1, 2,3,4, respectively, for $\beta_j$ close to $\beta(s,x)$.

Step 56. Multiply the quantities $\Psi_k(s, \beta(s,x))$, k=1,2,3,4, by the factors taken from equation (17) and add them up. This will give the quantity $$A(s, x) = \left(\frac{\partial}{\partial s}\frac{1}{|x - y(s)|}\right)\Psi_1(s, \beta(s, x)) + \frac{\beta_s(s, x) \cdot u(s, x)}{|x - y(s)|}\Psi_2(s, \beta(s, x)) + \frac{e_s(s, x) \cdot u(s, x)}{|x - y(s)|}\Psi_4(s, \beta(s, x)) + \frac{\beta_s(s, x) \cdot e(s, x)}{|x - y(s)|}\Psi_3(s, \beta(s, x)).$$

Step 57. Add the said quantity $A(s,x)$ to the image being reconstructed at the point x according to a pre-selected scheme (for example, the Trapezoidal scheme) for approximate evaluation of the integral with respect to s in equation (17).

Step 58. If the parameter value s corresponding to the CB projection, which is currently in computer memory, is close to a boundary point of the parametric interval $I_{PI}(x)$—either $s_b(x)$ or $s_t(x)$, then using interpolation find $$\frac{\Psi_1(s', \beta(s', x))}{|x - y(s')|}.$$

Here s' is either $s_b(x)$ or $s_t(x)$. Using the found value update the image being reconstructed at the point x according to equation (17).

Step 59. Go to Step 51 and choose a different reconstruction point x.

Step 60.

Step 61. Fix a reconstruction point x. If all the subsequent CB projections are not needed for reconstructing the image at this point, divide the value of the computed image at x by $-2\pi^2$ and display the image at x on the computer display 6 of FIG. 1. Repeat this step for all the reconstruction points.

Step 62. If not all the CB projections have been processed, go to Step 10 and load the next CB projection into computer memory. The algorithm concludes if the remaining CB projections are not needed for image reconstruction at any of the reconstruction points x or if there are no more CB projections to process.

EMBODIMENT THREE

For the third embodiment, two families of lines can be used in combination with either one CB projection in memory or with several CB projections in memory. We will first present the main reconstruction formula, and then describe the novel algorithm. Denote $$e_1(s, x) := \frac{[\beta(s, x) \times \dot{y}(s)] \times \beta(s, x)}{|[\beta(s, x) \times \dot{y}(s)] \times \beta(s, x)|}. \quad (19)$$

By construction, $e_1(s,x)$ is a unit vector in the plane through $y(s)$ and spanned by $\beta(s,x)$, $\dot{y}(s)$. Moreover, $e_1(s,x) \perp \beta(s,x)$. Given $y(s), s \in (s_b(x), s_t(x))$, $\check{s}(x)$, find $s_{tan} \in I_{PI}(x), s_{tan} \neq s$, such that the plane through $x, y(s)$, and $y(s_{tan})$ is tangent to $C_{PI}(x)$ at $y(s_{tan})$. This is equivalent to solving $$[(x-y(s_{tan})) \times (x-y(s))] \cdot \dot{y}(s_{tan}) = 0, s_{tan} \neq s. \quad (20)$$

Existence and uniqueness of the solution $s_{tan} \in I_{PI}(x)$ to (20) is shown in A. Katsevich "Theoretically exact FBP-type inversion algorithm for Spiral CT", which is accepted in January 2002 for publication in the "SIAM Journal on Applied Mathematics". It is also shown there that $s_{tan}(s,x)$ is smooth with respect to s on $(s_b(x), s_t(x))$, $\check{s}(x)$ and is made continuous on $[s_b(x), s_t(x)]$ by setting $$s_{tan}(s,x) = s_t(x) \text{ if } s = s_b(x),$$
$$s_{tan}(s,x) = \check{s}(x) \text{ if } s = \check{s}(x),$$
$$s_{tan}(s,x) = s_b(x) \text{ if } s = s_t(x). \quad (21)$$

Once $s_{tan} = s_{tan}(s,x)$ has been found, denote similarly to (19)

$$e_2(s, x) := \frac{[\beta(s, x) \times \Theta] \times \beta(s, x)}{|[\beta(s, x) \times \Theta] \times \beta(s, x)|}, \quad (22)$$

where $$\Phi = \text{sgn}(s-s_{tan}(s,x))\beta(s_{tan},x) \text{ if } s \in (s_b(x), s_t(x)), \check{s}(x),$$
$$\Phi = \dot{y}(s_{tan}) \text{ if } s \in \{s_b(x), \check{s}(x), s_t(x)\}. \quad (23)$$

By construction, $e_2(s,x)$ is a unit vector in the plane through $x, y(s)$, and tangent to $C_{PI}(x)$ at $y(s_{tan})$. In addition, $e_2(s,x) \perp \beta(s,x)$. The inversion formula is now as follows:

$$f = \frac{1}{2}(B_1 f + B_2 f), \quad (24)$$

where $$(B_k f)(x) := -\frac{1}{2\pi^2} \int_{I_{PI}(x)} \frac{1}{|x - y(s)|} \times \int_0^{2\pi} \frac{\partial}{\partial q} D_f(y(q), \cos\gamma\beta(s, x) + \sin\gamma e_k(s, x))\bigg|_{q=s} \frac{d\gamma}{\sin\gamma} ds, \quad (25)$$

$$k = 1, 2.$$

This formula was proven to be theoretically exact in A. Katsevich "Theoretically exact FBP-type inversion algorithm for Spiral CT", which was accepted in January 2002 for publication in the "SIAM Journal on Applied Mathematics".

Now we describe an efficient (that is, of the FBP type) implementation of inversion formula (24), (25). Denoting $$e_1(s, \beta) := \frac{[\beta \times \dot{y}(s)] \times \beta}{|[\beta \times \dot{y}(s)] \times \beta|}, \beta \in S^2, \quad (26)$$

rewrite $B_1 f$ as follows:

$$(B_1 f)(x) := \frac{1}{2\pi^2} \int_{I_{PI}(x)} \frac{1}{|x - y(s)|} \Psi_1(s, \beta(s, x)) ds, \quad (27)$$

$$\Psi_1(s, \beta) := \int_0^{2\pi} \frac{\partial}{\partial q} D_f(y(q), \cos\gamma\beta + \sin\gamma e_1(s, \beta))\bigg|_{q=s} \frac{1}{\sin\gamma} d\gamma. \quad (28)$$

Figure 12:
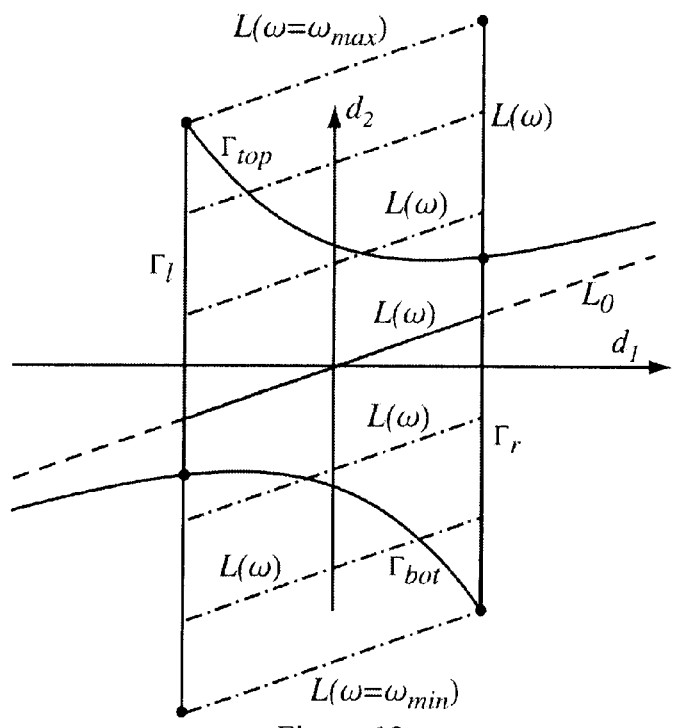
FIG. 12 illustrates the first family of lines used in Embodiment Three of the invention.

Let $\Pi(\omega), \omega \in R$, where R is the set of real numbers, denote the family of planes containing $y(s)$ and parallel to $\dot{y}(s)$. Intersections of $\Pi(\omega)$ with the detector plane generate a family of lines $L(\omega)$ parallel to $L_0$ (see FIG. 12). Fix any $\beta \in \Pi(\omega)$. By construction, vectors $\cos\gamma\beta + \sin\gamma e_1(s,\beta), 0 \leq \gamma < 2\pi$, belong to the same plane $\Pi(\omega)$. Recall that for convenience we think of vectors $\beta, e_1(s,\beta)$, and their linear combinations as if they are attached to $y(s)$. Let $\theta$ be a polar angle in $\Pi(\omega)$. Since $e_1(s,\beta) \cdot \beta = 0, |e_1(s,\beta)| = 1$, we can write:

$$\beta=(\cos\theta,\sin\theta), e_1(s,\beta)=(-\sin\theta,\cos\theta), \beta, e_1(s,\beta)\in\Pi(\omega). \quad (29)$$

Therefore, $$\left(\Psi_1(s,\beta)=\int_0^{2\pi}\frac{\partial}{\partial q}D_f(y(q),(\cos(\theta+\gamma),\sin(\theta+\gamma)))\bigg|_{q=s}\frac{1}{\sin\gamma}d\gamma,\right. \quad (30)$$

$$\beta\in\Pi(\omega).$$

Equation (30) is of convolution type. Hence, one application of FFT to the integral in equation (30) gives values of $\Psi_1(s,\beta)$ for all $\beta\in\Pi(\omega)$ at once. Calculation of $B_2 f$ can be arranged in a similar way. It follows from equation (20) that, apart from the condition $s_{tan}\in I_{Pf}(x)$, $s_{tan}$ actually depends only on s and $\beta(s,x)$. Therefore, we can write $$e_2(s,\beta):=\frac{[\beta\times u]\times\beta}{|[\beta\times u]\times\beta|}, u=u(s,\beta), \beta\in S^2, \quad (31)$$

$$\Psi_2(s,\beta):=\int_0^{2\pi}\frac{\partial}{\partial q}D_f(y(q),\cos\gamma\beta+\sin\gamma e_2(s,\beta))\bigg|_{q=s}\frac{1}{\sin\gamma}d\gamma, \quad (32)$$

$$(B_2 f)(x):=-\frac{1}{2\pi^2}\int_{I_{Pf}(x)}\frac{1}{|x-y(s)|}\Psi_2(s,\beta(s,x))ds. \quad (33)$$

Figure 13:
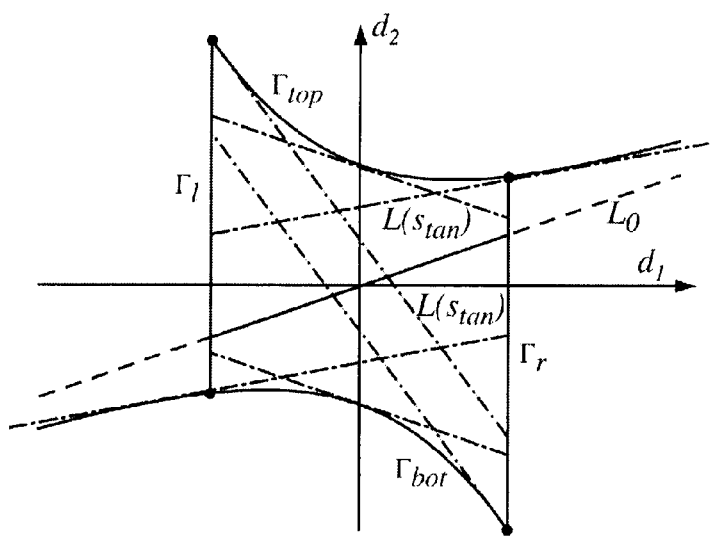
FIG. 13 illustrates the second family of lines used in Embodiment Three of the invention.

Fix $s_{tan}\in[s-2\pi+\Delta,s+2\pi-\Delta], s_{tan}\neq s$, and let $\Pi(s_{tan})$ denote the plane through y(s), $y(s_{tan})$, and containing $\dot{y}(s_{tan})$. If $s_{tan}=s$, $\Pi(s_{tan})$ is determined by continuity and coincides with the plane through y(s) and parallel to $\dot{y}(s)$, $\ddot{y}(s)$. The family of lines $L(s_{tan})$ obtained by intersecting $\Pi(s_{tan})$ with the detector plane is shown in FIG. 13. By construction, given any $x\in U$ with $\beta(s,x)\in\Pi(s_{tan})$ and such that $\hat{x}$ appears to the left (right) of the point of tangency $s_{tan}$ if $\hat{x}$ is above (below) $L_0$, then $s_{tan}$ used here is precisely the same as $s_{tan}$ provided by equations (20) and (21). The condition that we have formulated regarding the location of $\hat{x}$ relative to $s_{tan}$ and $L_0$ guarantees that $s_{tan}\in I_{Pf}(x)$. Since $e_2(s,\beta)\cdot\beta=0, |e_2(s,\beta)|=1$, we can write:

$$\beta=(\cos\theta,\sin\theta), e_2(s,\beta)=(-\sin\theta,\cos\theta), \beta, e_2(s,\beta)\in\Pi(s_{tan}). \quad (34)$$

Therefore, $$\left(\Psi_2(s,\beta)=\int_0^{2\pi}\frac{\partial}{\partial q}D_f(y(q),(\cos(\theta+\gamma),\sin(\theta+\gamma)))\bigg|_{q=s}\frac{1}{\sin\gamma}d\gamma,\right. \quad (35)$$

$$\beta\in\Pi(s_{tan}).$$

Equation (35) is of convolution type and one application of EFT gives values of $\Psi_2(s,\beta)$ for all $\beta\in\Pi(s_{tan})$ at once. After $\Psi_2(s,\beta)$ has been computed, we use only the portion of it that is located to the left (right) of the point of tangency $s_{tan}$ if $L(s_{tan})$ is above (below) $L_0$. In numerical implementation of equations (27), (30), and (33), (35) one can use bilinear interpolation to pass from a rectangular grid of points on the detector to points on the lines $L(\omega)$ and $L(s_{tan})$ and back. As suggested by equations (30) and (35), the points on $L(\omega)$ and $L(s_{tan})$ can be parameterized by polar angle in the corresponding plane.

Equations (27), (30), and (33), (35) demonstrate that the resulting algorithm is of the FBP type. First, one computes shift-invariant filtering of a derivative of CB projections using (30) for all required $\omega$: $\omega_{min}\leq\omega\leq\omega_{max}$ (cf. FIG. 12), and using equation (35)—for all $s_{tan}\in[s-2\pi+\Delta,s+2\pi-\Delta]$ (cf. FIG. 13). The second step is back-projection according to (27) and (33). Since $\partial/\partial q$ in equations (30) and (35) is a local operation, each CB projection is stored in memory as soon as it has been acquired for a short period of time for computing this derivative at a few nearby points and is never used later. Now we describe the algorithm in detail.

Step 10 is the Same as Step 10 in Embodiment One.
Step 20. Selecting the two sets of lines.
  Step 21. Choose a discrete set of values of the parameter $\omega$ inside the interval $\omega_{min}\leq\omega\leq\omega_{max}$ (see FIG. 12). This will give a collection of planes $\Pi(\omega_j)$ containing $y(s_0)$ and parallel to $\dot{y}(s_0)$.
  Step 22. Intersections of $\Pi(\omega_j)$ with the detector plane $DP(s_0)$ generates the first family of lines $L(\omega_j)$ parallel to $L_0$ (see FIG. 12).
  Step 23. Choose a discrete set of values of the parameter $s_{tan,j}$ inside the interval $[s_0-2\pi+\Delta,s_0+2\pi-\Delta]$.
  Step 24. For each selected $s_{tan}=s_{tan,j}$ consider the plane $\Pi(s_{tan})$ through y(s), $y(s_{tan})$, and containing $\dot{y}(s_{tan})$. If $s_{tan}=s$, $\Pi(s_{tan})$ is determined by continuity and coincides with the plane through $y(s_0)$ and parallel to $\dot{y}(s_0)$, $\ddot{y}(s_0)$.
  Step 25. The family of lines $L(s_{tan,j})$ obtained by intersecting $\Pi(s_{tan,j})$, selected in Step 24, with the detector plane $DP(s_0)$ is the required second family of lines (see FIG. 13). Step 30. Preparation for Filtering
  This step is essentially the same as Step 30 of Embodiment One. The minor differences are as follows. Here this step is used twice. The first time it is applied to the first family of lines $L(\omega_j)$ and gives the first processed CB data $\Psi_1(s_0,\beta_j)$.
  The second time it is applied to the second family of lines $L(s_{tan,j})$ and gives the second processed CB data $\Psi_2(s_0,\beta_j)$.
Step 40. Filtering
  The filtering step is also essentially the same as Step 40 of Embodiment One. The only difference is that here it is used twice. The first time it is used to convolve the first processed CB data $\Psi_1(s_0,\beta_j)$ with filter $1/\sin\gamma$ along lines $L(\omega_j)$ from the first family of lines giving the first filtered CB data $\Phi_1(s_0,\beta_j)$. The second time it is used to convolve the second processed CB data $\Psi_2(s_0,\beta_j)$ with filter $1/\sin\gamma$ along lines $L(s_{tan,j})$ from the second family of lines giving the second filtered CB data $\Phi_2(s_0,\beta_j)$.
Step 50. Back-projection
  The back-projection step is also essentially the same as Step 50 of Embodiment One. The only difference is that here Steps 51–56 are used twice. The first time they are used to back-project the first filtered CB data $\Phi_1(s_0,\beta_j)$. The second time they are used to back-project the second filtered CB data $\Phi_2(s_0,\beta_j)$.
  Step 57. Following equation (24), add the said contributions from the first and second back-projected CB data to the image being reconstructed at the point x according to a pre-selected scheme (for example, the Trapezoidal scheme) for approximate evaluation of the integrals in equation (25).
  Step 58 is the same as Step 58 in Embodiment One.
Step 60 is the Same as Step 60 in Embodiment One.
Other Embodiments of the invention are possible. For example, one can integrate by parts in equation (25) (similarly to what was done with equation (10)—see equation (17)), to get an exact FBP-type inversion formula which requires keeping only one CB projection in computer memory. The algorithmic implementation of this alternative embodiment will be very similar to the algorithmic implementation of Embodiment Two.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of reconstructing images from data provided by two dimensional detectors, comprising the steps of:

scanning an object in a spiral mode with two dimensional detectors with cone beam projections; and reconstructing an exact image of the scanned object in an efficient manner with a convolution based FBP (Filtered Back Projection) algorithm.

2. The method of claim 1, wherein the step of scanning includes the step of:

spiral scanning the object.

3. The method of claim 1, wherein the scanning step further includes the step of:

moving a table supporting the object through a rotational scanner.

4. The method of claim 1, wherein the step of reconstructing further includes the step of:

shift invariant filtering of each of the cone beam projections; and back projection updating the image of the scanned object.

5. The method of claim 1, wherein the step of reconstructing includes the steps of:

storing approximately 2 to approximately 4 cone beam (CB) projections in memory at a time; and using one family of lines for the step of reconstructing.

6. The method of claim 1, wherein the step of reconstructing includes the steps of:

storing 1 cone beam (CB) projection in memory at a time; and using one family of lines for the step of reconstructing.

7. The method of claim 1, wherein the step of reconstructing includes the steps of:

storing approximately 2 to approximately 4 cone beam (CB) projections in memory at a time; and using two families of lines for the step of reconstructing.

8. The method of claim 1, wherein the step of reconstructing includes the steps of:

storing 1 cone beam (CB) projection in memory at a time; and using two families of lines for the step of reconstructing.

9. A method of computing exact images derived from spiral computer tomography with area detectors, comprising the steps of:

(a) collecting data from a two dimensional detector during a scan of an object;

(b) identifying lines on said detector;

(c) shift invariant filtering said data along said lines with a convolution based FBP (Filtered Back Projection) algorithm;

(d) back projecting said filtered data to form a precursor of said image; and (e) repeating steps a, b, c, and d until an exact image of the object is completed.

10. The method of claim 9, wherein the scan includes an x-ray exposure of the object.

11. The method of claim 9, wherein the step (b) of identifying lines includes the steps of:

(bi) choose a discrete set of values of the parameter $s_2$ inside the interval $[s_0-2\pi+\Delta, s_0+2\pi-\Delta]$;

where $y(s_0)$ is the mid point of the CB projections currently stored in memory, $\Delta$ is determined by the radius r of the imaginary cylinder U inside which the patient is located (see FIG. 3): $\Delta = 2\cos^{-1}(r/R)$;

(bii) compute the vector $u(s_0, s_2)$ for each selected $s_2$ according to equations $$u(s_0, s_2) = \frac{(y(s_1) - y(s_0)) \times (y(s_2) - y(s_0))}{|(y(s_1) - y(s_0)) \times (y(s_2) - y(s_0))|} \operatorname{sgn}(s_2 - s_0) \text{ if } 0 < |s_2 - s_0| < 2\pi,$$

$$u(s_0, s_2) = \frac{\dot{y}(s_0) \times \ddot{y}(s_0)}{|\dot{y}(s_0) \times \ddot{y}(s_0)|} \text{ if } s_2 = s_0.$$

where, $y(s_0), y(s_1), y(s_2)$ are three points on the spiral related according to (4), (5);

$u(s_0, s_2)$ is a unit vector perpendicular to the plane containing the points $y(s_0), y(s_1), y(s_2)$;

$\dot{y}(s) := dy/ds$;

$\ddot{y}(s) := d^2y/ds^2$;

(biii) find a line for each $u(s_0, s_2)$ which is obtained by intersecting the plane through $y(s_0)$ and perpendicular to the said vector $u(s_0, s_2)$ with the detector plane $DP(s_0)$; and (biv) repeating steps (bi–biii), and forming a family of lines from a collection of the lines.

12. The method of claim 9, further including the step of (b5) preparing the data prior to the step (c) filtering step of:

(b5i) fixing a line $L(s_2)$ from the set of lines obtained in step (b);

(b5ii) parameterizing points on the lines by polar angle $\gamma$ in the plane through $y(s_0)$ and $L(s_2)$;

(b5iii) choosing a discrete set of equidistant values $\gamma_j$;

(b5iv) find the unit vector $\beta_j$ for each $\gamma_j$ which points from $y(s_0)$ towards the point on $L(s_2)$ that corresponds to $\gamma_j$;

(b5v) computer derivatives using the CB projection data $D_f(y(q), \Phi)$ for a few values of q close to $s_0$ using equation $(\partial/\partial q)D_f(y(q), \Phi)|_{q=s_0}$ for all $\Phi = \beta_j$;

(b5vi) store the computed derivatives; and (b5vii) repeat steps (b5i) to b5vi for all lines $L(s_2)$ identified step (b), in order to create processed CB data $\Psi(s_0, \beta_j)$ corresponding to the x-ray source located at $y(s_0)$.

13. The method of claim 9, wherein the back-projection step (d) includes the steps of:

(di) fix a reconstruction point x, which represents a point inside the object being scanned where it is required to reconstruct the image;

(dii) if $s_0$ belongs to $I_{PI}(x)$, then the said filtered CB data affects the image at x and one performs Steps (diii) to (dviii), if $s_0$ is not inside interval $I_{PI}(x)$, then the said filtered CB data is not used for image reconstruction at x and go back to step (di) and choose another reconstruction point. Here $I_{PI}(x)$ the PI parametric interval;

(diii) find the projection $\hat{x}$ of x onto a detector plane $DP(s_0)$ and unit vector $\beta(s_0, x)$, which points from $y(s_0)$ towards x;

(div) identify lines from family of lines and points on the said lines that are close to the said projection x̂, using equation $$(x-y(s_0)) \cdot u(s_0,s_2)=0, \ s_2 \in I_{PI}(x);$$

(dv) using interpolate find value of $\Phi(s_0,\beta(s_0,x))$ from $\Phi(s_0,\beta_j)$ for $\beta_j$ close to $\beta(s_0,x)$;

(dvi) compute contribution from filtered CB data to the image being reconstructed at the point x by dividing $\Phi(s_0,\beta(s_0,x))$ by $-2\pi^2|x-y(s_0)|$;

(dvii) add the contribution to the image being reconstructed at the point x according to a pre-selected scheme; and (dviii) go to step (di) and choose a different reconstruction point x.

14. The method of claim 9, further comprising the steps of:

storing approximately 2 to approximately 4 cone beam (CB) projections in memory at a time; and using one family of lines for the step of reconstructing.

15. The method of claim 9, further comprising the steps of:

storing 1 cone beam(CB) projection in memory at a time; and using one family of lines for reconstructing the exact image.

16. The method of claim 9, further comprising the steps of:

storing approximately 2 to approximately 4 cone beam (CB) projections in memory at a time; and using two families of lines for reconstructing the exact image.

17. The method of claim 9, further comprising the steps of:

storing 1 cone beam(CB) projection in memory at a time; and using two families of lines for reconstructing the exact image.

18. A computer tomography method for reconstructing images from data provided by detectors, comprising the steps of:

scanning an object in a spiral mode with detectors with cone beam projections; and reconstructing an exact image of the scanned object in an efficient manner with a FBP (Filtered Back Projection) algorithm, while storing at least one cone-beam projection(CB) at a time, and using at least one family of lines.

19. The method of claim 18, wherein reconstructing step is convolution based.

20. The method of claim 18, further providing the step of:

providing two dimensional detectors as the scanning detectors.

* * * * *

UNITED STATES PATENT AND TRADEMARK OFFICE
CERTIFICATE OF CORRECTION

| | | |
|---|---|---|
| PATENT NO. | : 6,574,299 B1 | |
| APPLICATION NO. | : 10/143160 | |
| DATED | : June 3, 2003 | |
| INVENTOR(S) | : Alexander Katsevich | |

It is certified that error appears in the above-identified patent and that said Letters Patent is hereby corrected as shown below:

Column 1, line 10, below first paragraph, insert

--STATEMENT REGARDING FEDERALLY SPONSORED RESEARCH OR DEVELOPMENT

This subject invention was made with government support under the National Science Foundation, federal contract number DMS9704285/DMS0104033. The government has certain rights in this invention.--

Signed and Sealed this
Eighth Day of March, 2011

David J. Kappos
*Director of the United States Patent and Trademark Office*